(12) United States Patent
Thistle et al.

(10) Patent No.: US 8,048,144 B2
(45) Date of Patent: Nov. 1, 2011

(54) PROSTHESIS FIXATION DEVICE AND METHOD

(75) Inventors: Robert Thistle, Bridgewater, MA (US); Kristian DiMatteo, Waltham, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 331 days.

(21) Appl. No.: 10/999,763

(22) Filed: Nov. 30, 2004

(65) Prior Publication Data

US 2006/0116754 A1     Jun. 1, 2006

(51) Int. Cl.
*A61F 2/82* (2006.01)
(52) U.S. Cl. ........................................ 623/1.16
(58) Field of Classification Search .............. 606/213; 623/1.36, 1.13–1.16
See application file for complete search history.

(56) References Cited

U.S. PATENT DOCUMENTS

| | | | |
|---|---|---|---|
| 4,216,776 A | 8/1980 | Downie et al. | |
| 5,478,354 A | 12/1995 | Tovey et al. | |
| 5,571,167 A | 11/1996 | Maginot | |
| 5,676,696 A | 10/1997 | Marcade | |
| 5,695,504 A | 12/1997 | Gifford, III et al. | |
| 5,709,713 A | 1/1998 | Evans et al. | |
| 5,755,770 A | 5/1998 | Ravenscroft | |
| 5,755,775 A | 5/1998 | Trerotola et al. | |
| 5,817,113 A | 10/1998 | Gifford, III et al. | |
| 5,876,448 A * | 3/1999 | Thompson et al. | 623/1.13 |
| 5,976,178 A | 11/1999 | Goldsteen et al. | |
| 5,984,955 A | 11/1999 | Wisselink | |
| 5,993,481 A | 11/1999 | Marcade et al. | |
| 6,030,415 A * | 2/2000 | Chuter | 623/1.13 |
| 6,165,212 A * | 12/2000 | Dereume et al. | 623/1.13 |
| 6,302,906 B1 | 10/2001 | Goicoechea et al. | |
| 6,325,823 B1 * | 12/2001 | Horzewski et al. | 623/1.16 |
| 6,387,105 B1 | 5/2002 | Gifford, III et al. | |
| 6,391,038 B2 | 5/2002 | Vargas et al. | |
| 6,395,019 B2 | 5/2002 | Chobotov | |
| 6,416,542 B1 | 7/2002 | Marcade et al. | |
| 6,451,034 B1 | 9/2002 | Gifford, III et al. | |
| 6,461,365 B2 | 10/2002 | Bolduc et al. | |
| 6,565,582 B2 | 5/2003 | Gifford et al. | |
| 6,579,311 B1 | 6/2003 | Makower | |
| 6,596,003 B1 | 7/2003 | Realyvasquez, Jr. et al. | |

(Continued)

FOREIGN PATENT DOCUMENTS

FR     2 772 257     6/1999

(Continued)

OTHER PUBLICATIONS

International Search Report for PCT International Application No. PCT/US2005/043406 mailed Mar. 29, 2006.

*Primary Examiner* — Ryan Severson
(74) *Attorney, Agent, or Firm* — Brooks, Cameron & Huebsch, PLLC

(57) ABSTRACT

A prosthesis anchor is adapted to convert a previously untreatable anatomy into a more typical and treatable condition. Preferably, the anchor is adapted to be transported endoluminally to a deployment site in a body lumen. The anchor includes a landing section for securing the anchor at a relatively fixed position in the lumen, and a docking section adapted to receive a mating prosthesis the landing section of the anchor may be permanently affixed to the lumen by a variety of mechanical and/or adhesive fixation means.

13 Claims, 4 Drawing Sheets

U.S. PATENT DOCUMENTS

| | | | |
|---|---|---|---|
| 6,599,302 B2 | 7/2003 | Houser et al. | |
| 6,623,494 B1 | 9/2003 | Blatter | |
| 6,626,938 B1 | 9/2003 | Butaric et al. | |
| 6,648,901 B2 | 11/2003 | Fleischman et al. | |
| 6,652,543 B2 | 11/2003 | Spence et al. | |
| 6,656,215 B1 | 12/2003 | Yanez et al. | |
| 6,682,540 B1 | 1/2004 | Sancoff et al. | |
| 6,682,541 B1 | 1/2004 | Gifford, III et al. | |
| 2001/0023369 A1 | 9/2001 | Chobotov | |
| 2001/0044647 A1* | 11/2001 | Pinchuk et al. | 623/1.13 |
| 2002/0004680 A1* | 1/2002 | Plaia et al. | 623/1.23 |
| 2002/0052643 A1* | 5/2002 | Wholey et al. | 623/1.13 |
| 2003/0009211 A1* | 1/2003 | DiCarlo | 623/1.13 |
| 2003/0074055 A1 | 4/2003 | Haverkost | |
| 2003/0074057 A1 | 4/2003 | Rosengart | |
| 2003/0083738 A1* | 5/2003 | Holman et al. | 623/1.35 |
| 2003/0093145 A1* | 5/2003 | Lawrence-Brown et al. | 623/1.21 |
| 2003/0130724 A1* | 7/2003 | DePalma et al. | 623/1.16 |
| 2003/0195614 A1* | 10/2003 | Ryan et al. | 623/1.16 |
| 2004/0044364 A1* | 3/2004 | DeVries et al. | 606/213 |
| 2004/0073238 A1 | 4/2004 | Makower | |
| 2005/0113905 A1* | 5/2005 | Greenberg et al. | 623/1.16 |

FOREIGN PATENT DOCUMENTS

| | | | |
|---|---|---|---|
| FR | 2 773 057 | | 7/1999 |
| WO | WO 99/34748 | | 7/1999 |
| WO | WO 02/41790 | * | 5/2002 |
| WO | WO 03/011182 A2 | | 2/2003 |
| WO | WO 03/011195 A2 | | 2/2003 |
| WO | WO 2004/096090 | | 11/2004 |

* cited by examiner

PROSTHESIS FIXATION DEVICE AND METHOD

BACKGROUND OF THE INVENTION

Many medical conditions are treated by the implantation of a prosthesis in a body lumen. Such conditions include vascular stenosis and aneurysms and such prosthesis include stents and stent grafts. Increasingly, such prosthesis are deployed by endoluminal transport from a site remote from the deployment site. Fixation of the prosthesis at the deployment site is necessary to avoid displacement of the prosthesis. Stents are elongated devices, typically of a tubular skeletal metallic structure, with substantial elasticity. Stents may be used to support intraluminal walls and to exert a radial force on a constricted portion of a lumen wall to open a lumen to near normal size.

A stent-graft typically includes tubular graft material affixed to the inside or outside of a stent and is delivered to the damaged site of a blood vessel via a catheter. Endoluminal stent-grafts, i.e. stent grafts delivered endoluminally, are often used to repair blood vessels affected by a variety of lesions such as stenoses or aneurysms. In the case of a stenosis, a stent provides an unobstructed conduit for blood, bypassing a diseased area of the vessel.

Once deployed in a body lumen, such as a blood vessel, stents and stent grafts have a tendency to move. Such movement may be caused by fluid flow at the deployment site and/or by changing body morphology. In the case of a stent graft, this may lead to leakage around the stent graft.

In some situations, such as in the case of abdominal aortic aneurysums (AAA) this problem is acerbated by the presence of diseased tissue at or near the end of the stent graft, near the renal arteries for example. In view of the foregoing, it would be desirable to have a more positive way of effectively retaining prostheses, such as stents and stent-grafts, particularly in a region of diseased tissue, and thereby more effectively preventing movement of the prosthesis and leakage around an end thereof.

SUMMARY OF THE INVENTION

One aspect of the invention provides a prosthesis anchor or fixation device, which may be implanted surgically but preferably is adapted to be transported endoluminally to a deployment site in a body lumen. The anchor is capable of being deployed and fastened to a lumen wall to receive a mating prosthesis. The anchor includes a landing section for securing the anchor at a relatively fixed position in the lumen. The anchor further comprises a docking section adapted to receive the mating prosthesis wherein the mating prosthesis extends into the anchor through one end thereof.

The anchor section may be fastened to the lumen wall by adhesives, staples, sutures, or any other positive fastening means, and thus may be attached in a relatively limited area of non-diseased tissue. Docking of a mating prosthesis in the docking station may then convert a previously untreatable anatomy into a more treatable condition.

The invention also comprises the combination of such an anchor with a mating prosthesis and a method of securing a prosthesis in a body lumen using such a combination.

It is to be understood that both the foregoing general description and the following figures and detailed description are exemplary, but not restrictive, of the invention.

BRIEF DESCRIPTION OF THE DRAWINGS

For a better understanding of the present invention and the various advantages thereof reference may be made to the following detailed description, and to the accompanying figures, in which common reference numbers identify similar elements in the various figures. In the figures.

DETAILED DESCRIPTION OF THE INVENTION

Figure 1:
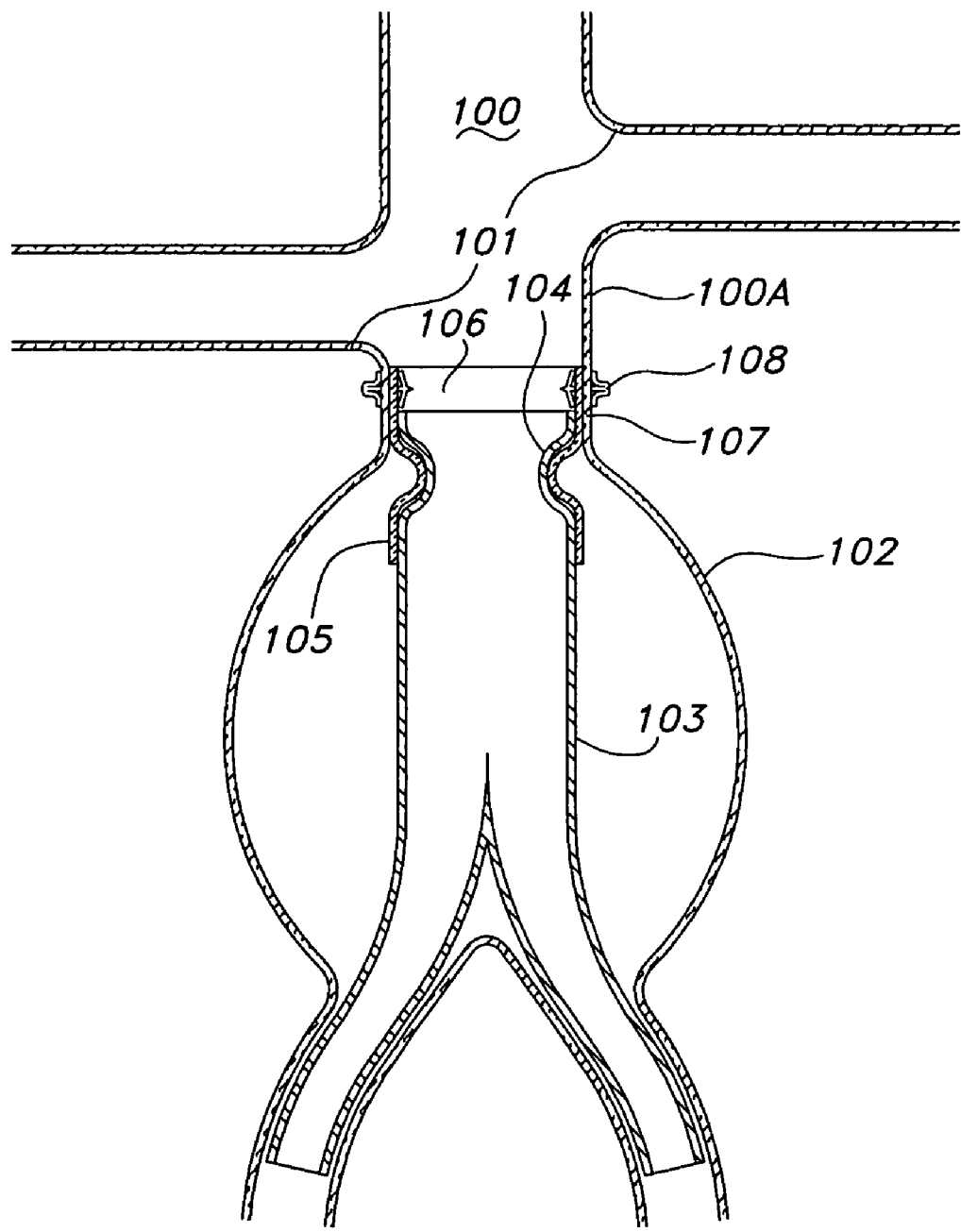
FIG. 1 depicts a section of an abdominal aorta in which is implanted a bifurcated stent graft retained by a pre-placed anchor-docking station.

As shown in FIG. 1, an abdominal aorta 100 includes an aneurysm 102, located below renal arteries 101. Disposed just below renal arteries 101, the upper end 104 of a bifurcated stent graft 103 is affixed to the short undiseased length 100a of aorta 100 between renal arteries 101 and aneurysm 102 by engagement with a ridge defining an hour glass mating with a similar configuration in a mating docking section 105 of anchor 106. Anchor 106 also includes a landing section 107. Landing section 107 is attached to the aortic tissue above aneurysm 102 by double flat head fasteners 108 (as disclosed for example in U.S. Patent Application 2004/0044364 A1). Such fasteners include a shaft adapted to penetrate the landing section and an adjacent lumen wall with a flat head on each end thereof. The upper end 104 of stent graft 103 is thus firmly retained in mating docketing section 105 of anchor 106, and thereby in aorta 100, notwithstanding the relatively small amount of healthy tissue in aorta 100 between aneurysm 102 and renal arteries 101.

Figure 2:
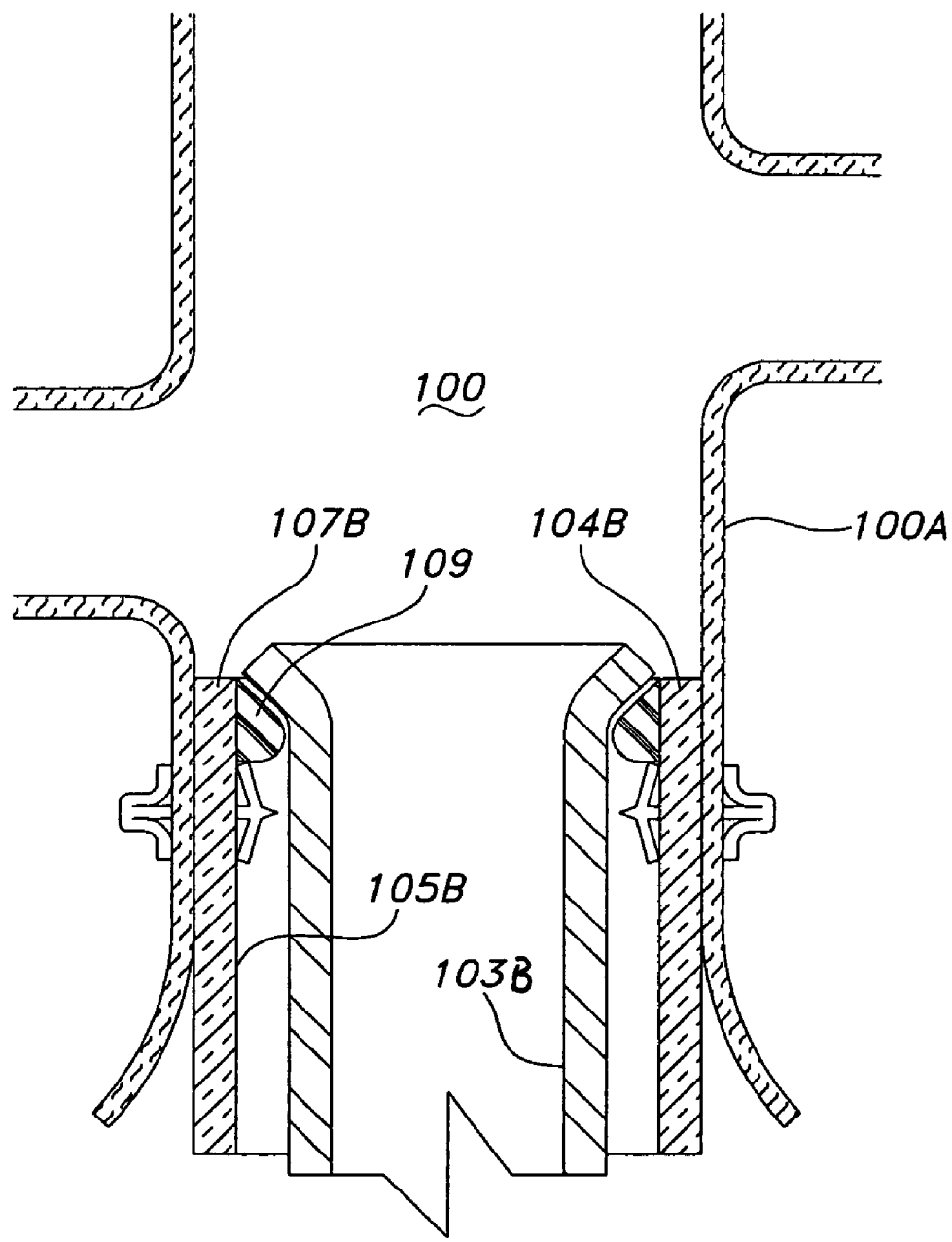
FIG. 2 depicts an alternative form of an anchor-docking station and mating stent graft.

Referring now to FIG. 2, there is shown an alternative form of anchor landing section 107. In this embodiment mating upper end 104B of stent graft 103B is self expanded to be force fit over a sealing ring 109 at the upper end of anchor docking section 105B causing sealing ring 109 to sealingly receive mating endoluminal prosthesis 103B.

Figure 1A:
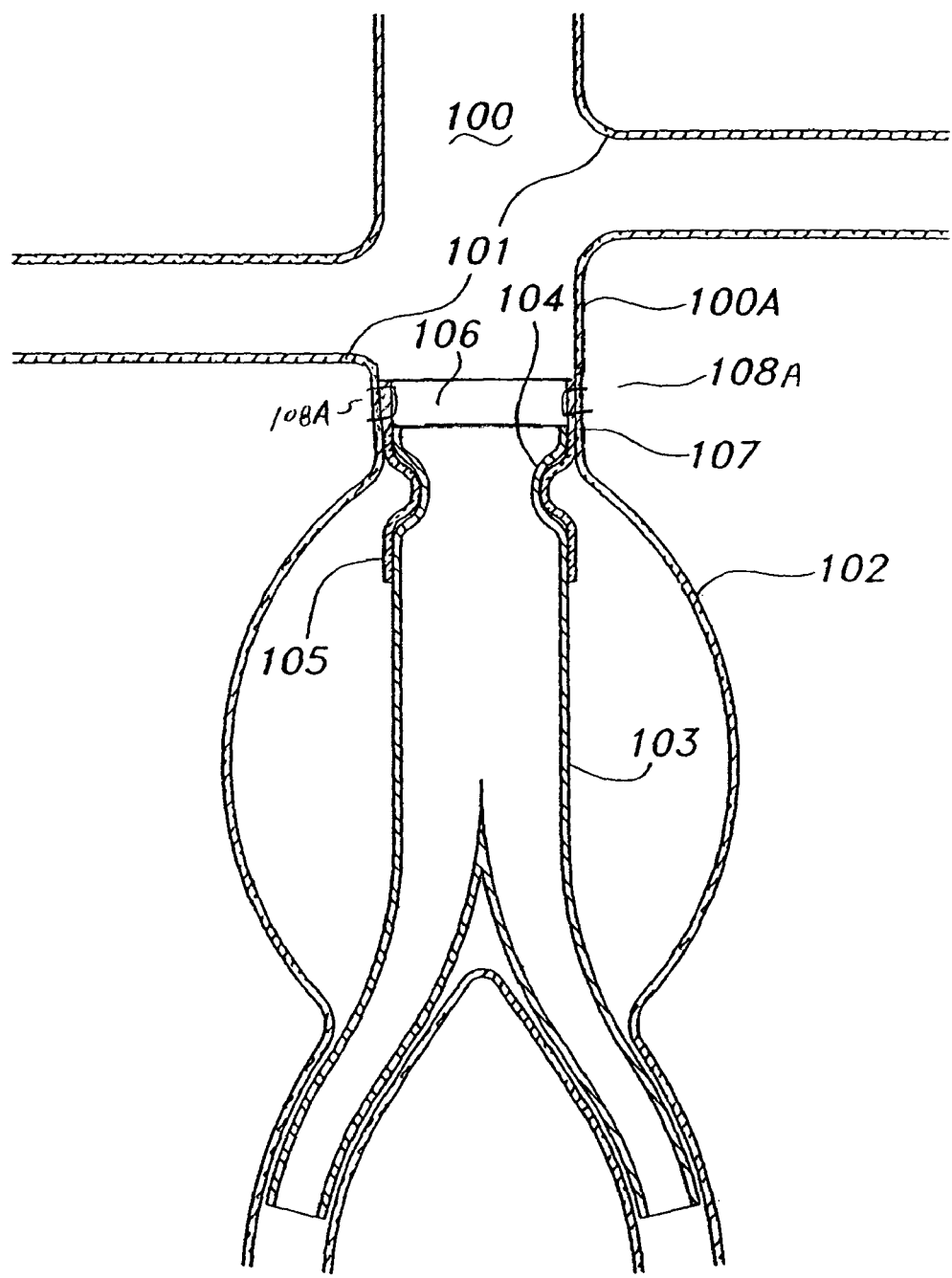
FIG. 1A depicts a first alternative form of a permanent fixation to affix the anchor-docking station to the abdominal aorta.
Figure 1B:
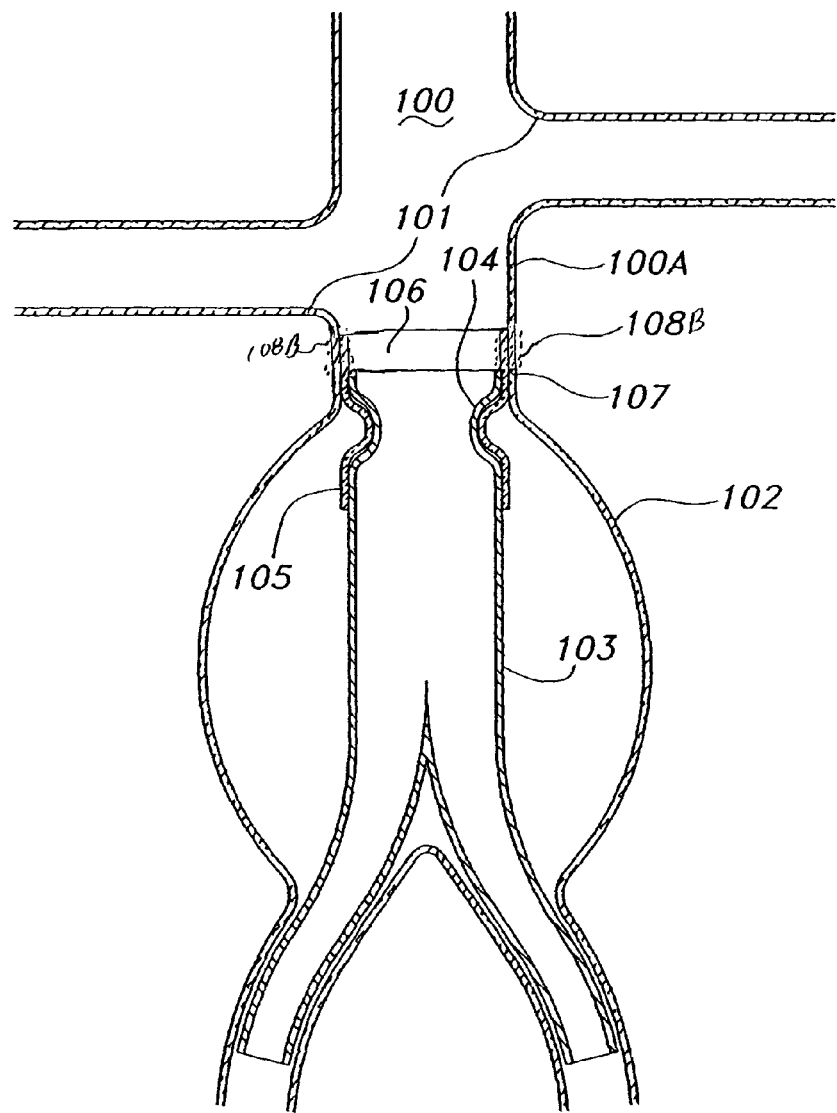
FIG. 1B depicts a second alternative form of a permanent fixation to affix the anchor-docking station to the abdominal aorta.

Other types of permanent fixations, by which a landing section of a prosthetic anchor may be secured to a lumen in which a mating prosthesis is to be deployed, may include any mechanical device comprising biocompatible material and adapted to secure an anchor element to a lumen. Thus, the forcefit frictional engagement of the ridged upper end 104 of stent graft 103 in docking section 105, shown in FIG. 1, or the sealing ring 109 shown in FIG. 2 may be used alone or in combination with each other or with sutures 108A (shown in FIG. 1A), staples 108B (shown in FIG. 1B), or with still other types of engagement such as biologic or chemical adhesives interposed between the lumen wall and the anchor landing section. Any of these types of engagements may also be used (alone or in combination) with some other type of engagement.

Sealing ring 109, as shown in FIG. 2, may comprise a solid elastomeric gasket made of silicone, polyurethane, or a similar material. In an alternative embodiment, sealing ring 109, may be an expandable annulus wherein once the prosthesis is placed in contact with it, the expandable annulus may be expanded to fill the space between the docking section and the prosthesis, thereby preventing either section of the device from moving relative to one another. A resinous or plastic solidifying material, which expands upon injection, as is discussed for example in U.S. Pat. No. 6,395,019 B2, may be used in such an expandable annulus.

Where an adhesive is used, the adhesive may be a pressure sensitive substance that reacts to the contact pressure between the docking section landing area and the lumen wall such that it becomes adhesive once deployment occurs. Still other types of adhesives, such as heat, radiation or chemically activated adhesives, may also be used.

The anchor may also be secured to the lumen wall by one or more barbs. For more secure fastening, at least two such barbs may be angularly disposed in opposing angular directions on the outer wall of a cylindrical anchor. By angularly disposed is meant that the barbs, while generally aligned with the axis of the anchor, are offset by at least several degrees, relative to the axis of the cylindrical anchor so that they exert circumferential resistance (in opposite circumferential directions) when an axial force tends to cause the anchor to migrate axially. Such oppositely directed barbs may also tend to resist circumferential migratory forces.

In as much as the anchor and mating prosthesis of this invention are best adapted for endoluminal placement, it will be apparent to those skilled in the art that, for that purpose, each would be adapted for endoluminal delivery. Specifically each would have a compressed configuration, in which they would be loadable and deliverable through a catheter introducer, and an expanded configuration, to which they would be converted on deployment, either by balloon expansion or by self expansion.

Although illustrated and described herein with reference to specific embodiments, the present invention is nevertheless not intended to be limited to the details shown. Rather, various modifications may be made in the details within the scope and range of equivalents of the claims and without departing from the spirit of the invention. For example, although illustrated and described herein with reference to AAA prostheses and stent graft applications, it should be understood that the apparatus and methods of this invention may be useful in any lumen, vascular or non-vascular, non-branched, bifurcated, or having multiple branches.

What is claimed:

1. A prosthesis anchor assembly comprising:
   an anchor having:
      a single landing section configured to be secured at a fixed position in a body lumen, the single landing section having a first diameter that is substantially constant along the entire length of the single landing section;
      a docking section extending from the single landing section, configured such that the single landing section and the docking section form separate sections of the anchor, and having a wall of the docking section wherein a first portion of the wall immediately adjacent the landing section extends radially inwardly and has a second diameter, smaller than the first diameter, thereby defining an inwardly extending radial protrusion, the wall further having a second portion, such that the first portion extends between the second portion and the single landing section, the second portion having a third diameter, the third diameter being the same as the first diameter in an expanded condition;
   a single-layer mating prosthesis having an expanded configuration with a wall including a ridge defining a similar configuration as the inwardly extending radial protrusion, the wall having a larger diameter portion at least one side of the ridge and a smaller diameter at the ridge, the ridge of the prosthesis being engaged by the inwardly extending radial protrusion of the docking section of the anchor such that longitudinal movement of the prosthesis is prevented; and
   a permanent fixation configured to penetrate the single landing section and the body lumen to fix the anchor to the body lumen such that the separate single landing section is the only section of the anchor configured to touch and be fixed to the body lumen because the first portion of the wall of the docking section extends radially inwardly and has a second diameter, smaller than the first diameter, thereby defining an inwardly extending radial protrusion.

2. The prosthesis anchor assembly of claim 1 wherein said single landing section comprises a section of said anchor adapted to be affixed to said lumen with said permanent fixation.

3. The prosthesis anchor assembly of claim 2, wherein said permanent fixation comprises a double flat head fastener with a shaft adapted to penetrate the single landing section and a wall of an adjacent lumen with a flat head on each end of the shaft.

4. The prosthesis anchor assembly of claim 2 wherein said permanent fixation comprises at least one staple.

5. The prosthesis anchor assembly of claim 2 wherein said permanent fixation comprises at least one suture.

6. The prosthesis anchor assembly of claim 1 wherein the docking section has an hour glass configuration.

7. The prosthesis anchor assembly and mating prosthesis combination of claim 1, adapted to delivered and deployed endoluminally.

8. The prosthesis anchor assembly and mating prosthesis combination of claim 1, adapted to be placed in an abdominal aorta below the renal arteries.

9. The prosthesis anchor assembly and mating prosthesis combination of claim 1, wherein each of said anchor and said prosthesis have a compressed configuration in which they are adapted to be loaded in a catheter for endoluminal deployment to a deployment site and an expanded configuration, wherein said anchor and said prosthesis are adapted to be converted from said compressed configuration to said expanded configuration upon deployment to said deployment site.

10. A method of securing a prosthesis at a deployment site providing a combination as recited in claim 9 and first deploying said anchor to the deployment site and fastening the anchor to a lumen wall at the deployment site, then deploying the prosthesis and securing it to the anchor.

11. A prosthesis and anchor assembly, said prosthesis and anchor assembly comprising:
   an anchor having:
      a single landing section adapted to be secured at a fixed position in a body lumen, the single landing section having a first diameter that is substantially constant along the entire length of the single landing section in an expanded condition;
      a docking section extending from and immediately adjacent to the single landing section, configured such that the single landing section and the docking section form separate sections of the anchor, and the docking section having an end portion having a constant second diameter in an expanded condition and an inwardly extending annular protrusion disposed between the single landing section and the end portion, the second diameter being the same as the first diameter in the expanded condition;
   a permanent fixation configured to penetrate the single landing section of the anchor and the body lumen to fix the anchor to the body lumen such that the separate single landing section is the only section of the anchor configured to touch and be fixed to the body lumen because the inwardly extending annular protrusion of the docking section is positioned immediately adjacent the landing section and extends radially inwardly and has a second diameter smaller than the first diameter; and a single-layer prosthesis having an expanded configuration with a wall including a ridge defining a similar configuration as the annular protrusion, the wall having a larger diameter portion at least one side of the ridge and a smaller diameter at the ridge, the ridge of the prosthesis being engaged by the inwardly extending annular protrusion of the docking section of the anchor such that longitudinal movement of the prosthesis is prevented.

12. A method of fixing a single-layer prosthesis to a body lumen with an anchor having a single landing section and a docking section extending from and immediately adjacent to the landing section, the docking section including an end portion having a constant first diameter in an expanded condition and an inwardly extending annular protrusion disposed between the single landing section and the end portion, and the single landing section having a second diameter that is substantially constant along the entire length of the single landing section in an expanded condition, the second diameter being the same as the first diameter in the expanded condition, the method comprising the steps of:

configuring the single landing section and the docking section to form separate sections of the anchor;

affixing the single landing section of the anchor to the body lumen such that the separate single landing section is the only section of the anchor configured to touch and be fixed to the body lumen because the inwardly extending annular protrusion of the docking section is positioned immediately adjacent the landing section and extends radially inwardly and has a second diameter smaller than the first diameter; and then engaging an inwardly extending ridge of the single-layer prosthesis with the inwardly extending annular protrusion of the docking section such that longitudinal movement of the prosthesis with respect to the anchor is prevented.

13. The method according to claim 12, wherein the affixing step comprises affixing the single landing section between an aneurysm in the body lumen and renal arteries extending from the body lumen.

\* \* \* \* \*